(12) United States Patent
Rathnam

(10) Patent No.: US 6,557,562 B2
(45) Date of Patent: May 6, 2003

(54) HAIR PERMING METHOD

(76) Inventor: Jayaseelan Rathnam, 6601 Arbordale Ave., Solon, OH (US) 44139-4103

(*) Notice: Subject to any disclaimer, the term of this patent is extended or adjusted under 35 U.S.C. 154(b) by 0 days.

(21) Appl. No.: 09/802,339

(22) Filed: Mar. 9, 2001

(65) Prior Publication Data

US 2003/0024542 A1 Feb. 6, 2003

(51) Int. Cl.[7] ............... A45D 24/00; A65D 7/06; A61K 7/13
(52) U.S. Cl. ............... 132/200; 132/206; 132/208
(58) Field of Search .................. 132/200, 206, 132/208, 211, 202, 203, 204, 205; 424/70.1

(56) References Cited

U.S. PATENT DOCUMENTS

| | | |
|---|---|---|
| 4,301,820 A | 11/1981 | Cannell et al. |
| 4,470,423 A | 9/1984 | Wajaroff |
| 4,572,220 A | 2/1986 | Hsiung et al. |
| 4,848,377 A * | 7/1989 | Bires et al. ............... 132/222 |
| 5,046,515 A | 9/1991 | Heinz et al. |
| 5,277,206 A | 1/1994 | Rose et al. |
| 5,352,443 A | 10/1994 | Kubo et al. |
| 5,378,454 A | 1/1995 | Burmeister |
| 5,424,062 A | 6/1995 | Schwan et al. |
| 5,570,708 A | 11/1996 | Samain |
| 5,655,552 A | 8/1997 | Samain |
| 5,988,180 A | 11/1999 | Bergstrom |
| 6,116,250 A | 9/2000 | Buheitel |
| 6,378,530 B1 * | 4/2002 | Rezvani et al. ............. 132/205 |

* cited by examiner

Primary Examiner—John J. Wilson
Assistant Examiner—Robyn Kien Doan
(74) Attorney, Agent, or Firm—Mark A. Watkins; Hahn Loeser & Parks, LLP

(57) ABSTRACT

The present invention is deemed to change the very perming concepts and methods that have been used for decades. This new invention relates to the art of permanent waving of hair and reveals an innovative new perming system particularly for the professional salon industry and also for the retail home perm industry. The innovative techniques and concepts of perming with ultra gentle formulations and very short processing times will offer many great safety benefits for the salon clients, hairdressers, environment, and the perm industry. The new invention is primarily designed and focused on dramatically reducing the perming chemicals, the processing time, and the malodor associated with perming by 50 to 75% of the conventional perming products. Achieving a superior perm result using the mildest perm products and shortest processing time in the safest way with least damage to the hair is the highlight of this invention.

51 Claims, No Drawings

HAIR PERMING METHOD

TECHNICAL FIELD

The present invention is directed to a method of permanently waving hair. More specifically, the present invention is directed to a method of permanently waving hair using very short processing times and very low concentrations of treatment chemicals.

BACKGROUND

Human hair is made up of selected keratin amino acids. The inner part of hair consists of bundles of spindle-shaped protein fibers that make up the cortex. The cortex is surrounded and protected by a shield consisting of multiple layers of scales called cuticles. Water is one of the main components of hair, which provides pliability, manageability, natural feel and look. Healthy hair contains about 10% moisture in it. Hair treated repeatedly with permanent colors, highlights, bleaches, and perms tends to have less moisture in it. Lack of moisture in hair will result in dryness, dullness, harshness, breakage, static flyaways, etc.

When hair is in contact with water, it can absorb a considerable amount of water due to the inherent porosity of hair. Untreated normal hair can absorb water up to an additional 20 to 30% of the weight of hair, depending on the person's origin, health, food, climate, etc. Permed, tinted and bleached hair types can absorb water up to an additional 30 to 50% of the weight of hair, depending on the level of damage or porosity created in hair by the chemical services. Hair can get saturated with water on contact in about 15 to 45 minutes. The ease of saturation depends on the condition and openings in the outer cuticle layers which protect hair. The hair gets saturated with water quickly if the outer cuticles are damaged, ruptured or erupted, allowing water to penetrate easily. The presence of cysteic acid in and around hair also induces absorption and saturation of hair with water.

Permanent waving and the art of creating a permanent curl in straight hair through waving products are well known to the perm industry. Perming or waving action takes place in the cortex of hair where the cross-linking cystine is present. Cystine is the main amino acid involved in perming. Breaking of the disulfide bond of cystine into half-cystine units is the first step in perming (reduction) that is achieved by processing the hair that is wound onto a perm-rod with the waving lotion containing thio compounds such as thioglycolic or thiolactic acids, salts or esters, cysteine and its derivatives, cysteamine and its derivatives, inorganic sulfites and bisulfites, etc. The broken half-cystine units slowly tend to rearrange and align according to the shape of the perm-rod during the time of processing and also while rinsing away the waving lotion from hair. Relinking of the aligned half-cystine units and restoring of the original hair with a curl configuration is the second step (oxidation) that is achieved by a neutralizer.

The rate of perming action depends on the type of waving formulation, the amount or concentration of waving ingredients reacting with the disulfide bond of cystine in hair, the time of reaction and the conditions of reaction, like processing at room temperature or under a dryer, processing with or without the plastic cap, etc.

Prior to a conventional perming, the hairdresser gives one or two shampoos to the perm-client to remove dirt and coatings caused by styling products on the hair. Similarly, home permanent users also shampoo hair prior to wrapping. The hair is then towel blotted enough to have the right dampness to wrap on to the perm-rod with ease. Water is frequently misted onto the hair to maintain the right moisture in the hair while wrapping. After the completion of wrapping, a final mist of water also is given to make sure that the wound hair is uniformly moist. Depending on the length and density of the hair, it takes about 30 to 45 minutes per person for shampooing and wrapping. This means that by the above wrapping procedure, the hair to be permed is in contact with water for about 30 to 45 minutes. Thus, the wrapped hair gets saturated in and around with a good amount of water even before the application of perming products to the hair. At this stage the waving lotion is applied to the wrapped hair.

Several problems with prior art perming methods may be identified. These problems generally originate in the typical amount of water present in the wound hair to be permed. These problems include:

1. Waving lotion applied to wrapped hair that is saturated with water has a hard time penetrating through the cuticles into the cortex. The waving lotion reaching the ends of hair through osmosis also will be delayed by this absorbed water.
2. The delayed penetration of waving lotion causes spillage and wastage of waving lotion while applying to the wound hair that is saturated with water because hair cannot hold any more product beyond the limit.
3. Spilling of the strong waving lotion can cause skin contact, which can create allergic reactions, itching, redness, etc.
4. The delayed penetration of waving lotion unnecessarily delays the perming action and lengthens the processing time.
5. While waiting to penetrate through the cuticles, the waving lotion keeps reacting with the outer cuticles for an extended period of time causing cuticle damage. If the cuticles are very compact and closed as in normal untreated hair, the penetration time is much longer. This means that the waving lotion will attack the cuticles for a much longer time. On the contrary, if the cuticles are already damaged and open as in the case of bleached, highlighted, and repeatedly tinted hair types, the lotion penetration will be somewhat faster. Still, a lot of cuticle damage can occur on such fragile hair types, which are vulnerable to attack.
6. Besides the delay in lotion penetration, the applied waving lotion also gets diluted or weaker in strength by the water loaded in and around the hair.
7. To compensate for the delayed penetration, spillage, and weakening of waving lotion caused by the saturating water, a very strong and aggressive waving lotion, a long processing time and very often, heat activation become necessary for the conventional perms in order to produce a satisfactory perm result.
8. The combinations of high strength waving lotion, long processing times and heat activation cause hair damages, safety problems and strong malodor in the salon.

It would then be desirable to have a new perming method that improves permanent waving of hair as compared with prior art methods.

SUMMARY

The present invention includes various concepts, techniques, formulations and related products for an innovative perming system, to achieve desirable perm results in a safe way. The present invention also discloses solutions to eliminate many negatives of conventional perming. Included are benefits of the perming method of the present invention to the environment, perm-clients, hairdressers, and manufacturers. The following objects of the invention are new and different from that of conventional perming:

1. The present invention enables the presently used waving ingredient groups like thioglycolates, thiolactates, bisulfites, natural cysteine and its derivatives, cysteamine and its derivatives, and the combination of the above mentioned groups to provide great perm results in a very short time at a concentration or strength that is about 50 to 75% less than the conventional waving lotions.
2. The present invention maximizes the benefits by virtually removing or minimizing all the negatives associated with conventional perming. To correct the problems of delayed penetration, dilution and spilling of waving lotion in the conventional perming, the new invention recommends application of waving lotion to the wound hair that is dry or essentially dry. This way, the lotion penetrates at once without any restriction into the cortex of hair, evenly from root to end with least spillage, wastage or dilution. The ultra mild waving lotion will be able to do the perming most effectively and evenly in a very short time at room temperature without any heat activation. The benefits of ultra mild lotion, least spilling, very short room temperature processing and very short lotion contact time with the scalp and hair means that it is the safest perming for the client and safest and least damaging treatment for the hair.
3. Similarly, the present invention enables the regularly used oxidizing or neutralizing ingredients like hydrogen peroxide or sodium bromate to provide great perm results at a concentration that is about 50 to 60% less than the conventional neutralizers on the market.
4. The optional perm enhancer of the invention which is designed and formulated with selected surfactants, polymers, chelators, conditioners, moisturizers, proteins, hair nutrients, etc. will enhance perming in many ways.
5. The built-in cleansing and chelating systems in both the waving formulations and the perm enhancer will eliminate the need for shampooing prior to perming. (Excessive minerals or coating build-ups may need appropriate treatment or shampooing prior to perming.)

These and other objectives of the present invention will become apparent to the skilled practitioner upon reading the following specification and claims.

DESCRIPTION

In conventional perming, hair is shampooed once or twice, towel-blotted enough to have the right dampness and then wrapped onto the perm-rod. At this stage, the amount of this saturating water is rather large, which will dilute the applied waving lotion to a considerable level. Since the wound hair goes over the perm-rod many times depending on the hair length and the rod size, the dilution will not be instantaneously uniform from the root to the end of the wrapped hair. This dilution or weakening of waving lotion leads to a longer processing time. In addition, this situation creates a need for a much stronger lotion for the conventional perming not only to compensate for the dilution of waving lotion, but also for the spillage of waving lotion and the delayed penetration of the lotion due to the saturating water in and around hair.

As further described herein, shampooing and wrapping of hair during conventional perming saturates hair with water, which obstructs the penetration of the applied waving lotion, causes spillage and also dilutes or weakens the waving lotion. To avoid these problems, the method of the present invention does not require shampooing of hair that is reasonably clean prior to wrapping. If the hair is heavily coated with styling products or loaded with minerals, hair should be given a cleansing treatment or multiple shampoos and dried well using a blowdryer or diffuser prior to wrapping or dried well using a salon dryer after wrapping.

Various tools or devices for wrapping may be used with the methods of the present invention. These wrapping devices include but are not limited to (i) regular penn-rods for firmer and tighter or softer curls (ii) Velcro rollers or plastic nets for softer curls. The regular penn-rods and end papers can be used. The perm-rods, which facilitate rinsing and air circulation will be preferred. Likewise, end papers with small perforations will be preferred because they will help rinsing and air circulation, especially at the ends of the wound hair to remove moisture evenly from root to end during the creep step. A plurality of wrapping devices is used in penning hair, the number of wrapping devices depending upon various factors including the length of hair, texture, etc. Typically, about 40–50 perm rods would be used to perm a head of hair.

Hair may be wrapped dry or essentially dry, with a minimum of water or other forms of moisture such as the enhancer described in more detail herein. By essentially dry, it is meant that while the hair may contain some moisture, the moisture is only that which may be retained by the hair at equilibrium with the ambient air, or a some small amount that is added to control the hair and prevent static fly away and aid in combing the hair. It is much less moisture than would be present in hair subsequent to shampooing, rinsing and towel drying the hair, and is generally significantly lower than the point at which hair is saturated with water. Generally, essentially dry is meant to include all of the added moisture contents of hair that are about 10 percent by weight moisture or less. At this moisture level, hair is manageable and easily combed or wrapped, but is not soaked and therefore does not contain a moisture content sufficient to cause significant delay in penetration of waving lotion or significant dilution of waving lotion.

Thus, to prevent static flyaway during wrapping, water or other forms of moisture may be added to the hair in small amounts by misting or otherwise applying. The amount of moisture added will generally be small and the hair will remain in an essentially dry state while wrapping and before application of the waving lotion.

While hair may be wrapped dry or essentially dry with a minimum of plain water, an optional perm enhancer solution may be utilized during the wrapping step instead of or in addition to plain water. There are many benefits when the perm enhancer is used for wrapping. Untreated normal hair is hydrophobic in nature and tends to repel the wetting of water or water solutions without good wetting agents. The hydrophobicity of hair is due to the very chemical nature of the cuticle, which is made up of a special blend of keratin amino acids, especially the insoluble cystine, and also due to a thin layer of protective oil on the hair. Besides the hydrophobicity, the cuticles are compact and lay flat especially for normal hair, making it hard for the waving lotion to wet and then penetrate into the hair. Wetting can be achieved on repeated applications, but that will result in lotion spillage. The perm enhancer containing wetting, moisturizing, setting, conditioning, protecting, chelating and cleansing ingredients for easy combing and wrapping, uniform setting, quick wetting and penetration may be used advantageously to get even and optimum curl results.

The perming method of the present invention includes the following options to wrap hair: (1) most preferably, the hair can be wrapped onto the perm-rod or Velcro roller easily, misting the perm enhancer sparingly and evenly to the essentially dry hair up to about 10% of the weight of hair. This will offer many benefits to the hair. (2) Hair can be wrapped on to perm-rods or Velcro rollers misting water sparingly and evenly to the essentially dry hair up to about 10% of the weight of hair. There may be some difficulty in combing and wrapping when water misting is used. (3) The dry hair can be wrapped onto rods or Velcro rollers as such. There will be static, flyaway problems and also difficulty in wetting, combing and unevenness in wrapping when dry hair is wrapped as such. Therefore, in one embodiment the use of enhancer for wrapping achieves desirable perm results.

It is desirable to mist an optimum amount of perm enhancer or water to the hair for wrapping. If an excess amount is used, a weaker curl may result. In that event, after the completion of wrapping, the client can be placed under a salon dryer at medium setting for about 5 to 10 minutes to remove the excess moisture from the wrapped hair. Instead of a dryer, a diffuser or any other heating device also can be used for the same purpose without disturbing the wrapped hair. A salon dryer is preferred for even results. There is no need for any drying if the right amount of moisture (less than about 10% of the weight of the hair) is left in the hair. The wrapped hair must only be slightly moist but not wet.

The ultra gentle waving lotion used in the present invention is applied evenly to the top of all the wound hair first, then to the bottom, and finally to the middle of each wound hair. A cotton strip can be advantageously used, gently touching the wrapped hair while applying to contain lotion.

The waving lotions that may be used include all those that are well known in the art, including aqueous waving lotions suitable for alkaline perms, acid perms, perms having neutral pH, and perms using buffered alkaline waving lotions. Waving lotions generally contain one or more reducing agents such as thioglycolic or thiolactic acids and their derivative salts and esters, cysteine and its derivatives, cysteamine and its derivatives, inorganic sulfites, and bisulfites. Suitable waving lotions for the present invention include about 1 to about 12 percent by weight, as thioglycolic acid, of at least one reducing agent. Alternatively, the waving lotion may contain from about 1 to about 8 percent by weight, as thioglycolic acid, of at least one reducing agent. The waving lotion also contains alkaline ingredients such as ammonium hydroxide, sodium hydroxide, monoethanolamine, borax, ammonium carbonate, and ammonium bicarbonate. The waving lotion may contain alkaline ingredients in a total concentration ranging from about 0.02 to about 1 percent by weight, expressed as ammonia. Alternatively, the waving lotion may contain a total concentration of alkaline ingredients of from about 0.02 to about 0.7 percent by weight, expressed as ammonia. For waving lotions suitable for alkaline perms or perms having a neutral pH, the pH of the waving lotion is in a range of about 7 to about 9.5. For waving lotions suitable for acid perms, the pH is in a range of about 6.5 to about 8.5. Additionally, for waving lotions suitable for acid perms, from about 1 to about 10 percent by weight of glyceryl-monothioglycolate (GMT) is used. Generally, all waving lotions may contain one or more of various additives including chelating agents, cleansing herbs, anionic surfactants, amphoteric surfactants, nonionic surfactants, buffering agents, proteins, botanical extracts, amino acids and fragrances.

A processing cap may be used to cover all the wound hair to achieve desirable results. A cap may not be needed when fragile hair types are processed instantly giving a "zero" processing time or using very short processing times of 1 or 2 minutes.

After securing the cap, the hair is processed at room temperature. Heat activation is optional; room temperature processing is preferrable for safety and comfort. The processing times for the method of the present invention are typically much shorter than those typically used in conventional perming. The processing times with waving lotion using the method of the present invention are from about 0 to about 6 minutes for normal hair, from about 0 to about 5 minutes for tinted hair, and from 0 to about 3 minutes for bleached hair. Generally, no more than about 20 minutes, at most, is required for processing the hair with waving lotion. Alternatively, no more than about 10 minutes is required for processing the hair with waving lotion. This compares with typical salon processing times using conventional methods of about 20 to about 30 minutes for normal hair, from about 10 to about 20 minutes for tinted hair, and from about 5 to about 15 minutes for bleached hair.

The processing times for the present invention are considerably shorter than that of the conventional perms. The processing time will generally depend on, among other considerations, the strength of the waving lotion and the type of curl desired. Very good curl results can be achieved using a processing time of about 3 minutes or less for retail home permanents.

After processing with waving lotion, a thorough warm-water rinse is given for about 3 to about 5 minutes to the hair that is still wound onto perm-rods. After a thorough blotting with cotton and paper towels, misting of a pre-conditioner to the well-blotted hair prior to or after the creeping is optional. The pre-conditioner provides extra conditioning to dry, coarse hair types.

The client is then placed under a preheated dryer to creep at medium setting (50–60° C.) without a cap for about 5 to about 15 minutes, depending on the length and density of hair. Creeping creates a change in shape as a result of constant stress and higher temperature. The processed hair on the rod is at constant stress and the dryer heat enhances the realignment of the half-cystine units for the most efficient relinking of the sulfur-sulfur bonds to give a superior curl configuration, and also removes about 35 to about 40% of the moisture from the processed hair for instant and complete neutralization. The degree of realignment depends on the right temperature and the creep time. This beneficial realignment, or creep step is generally not used in conventional perming. The invention recommends the following creep times for desirable curl results:

about 10 minutes for average hair density and length (4–8 inches)

about 15 minutes for very dense or very long hair (over 8 inches long)

about 5 minutes for sparse or very short hair (less than 4 inches long)

After the creep, the wrapped hair is left to rest for about 2 minutes to equilibrate the moisture and temperature of hair from root to end prior to neutralizing.

Heat radiating heating lamps and roller ball or a diffuser also may be used for creeping instead of a dryer. Use of a salon hair dryer is desirable because of its typical availability in salons and because heating and moisture removal will be reasonably uniform with a dryer.

Generally, it has been found that a 10-minute creep for sparse (a section of hair that weighs about 1 gram) or short hair (about 4 inches or shorter) is excessive because the percentage of moisture removed from hair will be over 50% and possibly the amount of air neutralization introduced also will be too high. Consequently, the curl level and curl longevity both will drop considerably if the creep time is excessive. For desirable results, the following conditions and timings for sparse and short hair are used: (1) 5-minute creep without a cap under a dryer at medium setting (2) 7-minute creep without a cap under a dryer at low setting (3) let the client rest at room temperature without a cap for 30 to 40 minutes. These creep times and conditions provide desirable alignment and amount of moisture removal (35 to 40%) from the processed, damp hair for an instant neutralization without much air neutralization occurring simultaneously.

The percentage of moisture removed during creep for both normal density and sparse hair varies slightly depending on the perm-rod size. A medium size perm-rod, having a diameter of 1.15 cm removes about 1% more moisture while a large size perm-rod, having a diameter of 1.46 cm removes about 2% more moisture than the small size perm-rod, having a diameter of 0.83 cm. These small differences are apparently due to the area of the wrapped hair on the rod, which is exposed to heat during the creep step. But these differences in moisture removal are not sufficient to make any difference in curl results. A "cold" or "air-only" setting of a dryer also can be used by letting the client sit under a dryer. The cold air blowing on the damp hair for about 15 to about 20 minutes may remove enough moisture but the cold air will be uncomfortable for the client. The alignment obtained using cold air is typically inferior to that obtained with heat.

The curl stabilization ("creep") step prior to the actual neutralization is effective to achieve a better realignment of broken disulfide bonds and better rebonding to provide firmer, springier and lasting curls. The "creep" step also removes about 35 to 40% of the moisture from the processed damp, hair in 10 minutes, de-swells hair and brings the half-cysteine units closer for better realignment, and better and faster neutralization. The ten-minute creep time under a dryer without a cap, for average hair length and density is most favorable for the following reasons: (1) 10 minutes is a reasonably short and affordable time in a salon. (2) 10 minutes under a dryer should not be uncomfortable for a client. (3) 10 minute "creep" creates an optimum amount of moisture loss, realignment, and air neutralization for an effective instant neutralization to provide long lasting, great curls. (4) Longer creep times like 20 to 60 minutes favorably remove about 50 to 80% of moisture, which is good for instant neutralization, but a lot more air neutralization occurs in processed hair which adversely affects the curl levels and longevity. Too much air neutralization seems to create enough, but to some extent a loose rebonding in hair, which renders actual neutralization somewhat ineffective. The curl comes out weaker and relaxes faster than creeping for 10 minutes without a cap under the dryer.

A creep study was done using a processing cap and caps with pinholes up to about 60 minutes time. Best results were achieved when creeped with a cap for 60 minutes under a dryer at medium setting. It was noticed that about 40% of moisture in the damp hair distills out of the damp hair and deposits on the cap in 60-minute creeping. Thus, hair becomes partly dry similar to the hair creeped for about 10 minutes without a cap, and makes instant neutralization equally effective.

The processed hair that was creeped identically with a cap for 60 minutes, but not neutralized also gave reasonably good curls with slightly less curl longevity, yet better than conventional curls. When creeped with a cap, the amount of air neutralization occurring in processed hair will be limited because the cap will restrict airflow. But an enhanced realignment achieved by the long 60-minute creep time and the dryer heat is mainly responsible for such curl results without the neutralization. Creeping for 60 minutes with a cap under a dryer is not practical in a salon and also will not be comfortable or safe for the client.

Generally, creeping the hair in the presence of air will result in a moisture reduction of about 20 to 80 percent. Alternately, about 30 to 50 percent moisture reduction gives desirable results.

The ultra gentle neutralizer is applied the same way the waving lotion is applied as described earlier to the creeped hair still on the perm-rods. Application of neutralizer to a full head of hair takes about 3 minutes. The neutralizer penetrates into the partially dry hair instantly, and the rebonding or oxidation occurs instantly, so there is no need for additional waiting time besides the about 3-minute application time of the neutralizer. In comparison, conventional neutralizing requires about 5 minutes of waiting time to enable the neutralizer to penetrate into the wound damp hair. Effectively, the waiting time for the method of the present invention is essentially zero minutes, since in effect some time may elapse between final application of the neutralizer and final removal of the perm rods and rinse. However, no time is required for this waiting period.

The neutralizer used generally contains ingredients well known in the art. The neutralizer, or neutralizing lotion, is an aqueous solution of an oxidizing agent. The oxidizing agent may include hydrogen peroxide, sodium bromate, potassium bromate, or sodium perborate, among others. Hydrogen peroxide may be used in a concentration of from about 0.5 to about 3 percent by weight. Alternatively, the oxidizing agent is used in a concentration of from about 0.8 to about 1.2 percent by weight, at a pH of about 2.6 to about 3.6. Oxidizing agents other than hydrogen peroxide may be used at concentrations of similar oxidizing strength, as would be apparent to one of skill in the art.

After neutralization, the perm-rods are gently removed from the hair, and the left-over neutralizer is applied to the ends of curled hair and crunched gently for about a minute to be doubly sure of a complete neutralization. The curled hair is then thoroughly rinsed with lukewarm water for about 3 to about 5 minutes.

Optimized curls with excellent spring, depth, feel, and longevity are obtained using the methods of the present invention. The wound hair is maintained at an almost dry, or essentially dry, stage while applying the waving lotion and partially dry for the neutralizer to enable rapid penetration of product into the cortex. The ultra gentle waving lotion and neutralizer have less than half the strength of a conventional waving lotion and neutralizer, yet effective and safe perming is obtained in less than one-fourth of the processing time taken by conventional perms.

While in one embodiment the present invention is described as including the steps of wrapping essentially dry hair onto wrapping devices, applying waving lotion, processing the hair, creeping, and neutralizing, the methods of the present invention are not so limited. As will be appreciated by one of ordinary skill in the art, the steps of wrapping, applying the waving lotion, and processing are most essential to the invention. While some form of neutralization is generally desirable, creep may be used instead of or in addition to neutralization to obtain desirable results. The creeping and neutralizing steps may of course both be implemented in a most successful perm using the present invention, but useful results may be obtained using creep alone, neutralization alone, or a combination of creep and neutralization, in addition to the essential steps of wrapping essentially dry hair onto wrapping devices, applying waving lotion, and processing the hair.

The perm enhancer may be formulated as an aqueous combination of one or more additives including surfactants (anionic, cationic, nonionic or amphoteric), naturally derived or synthetic polymers (anionic, cationic or nonionic), amino acids, botanical extracts, proteins from vegetable or animal sources, conditioning, moisturizing and chelating agents. The total concentration of additives in the enhancer is from about 0.1 to about 5 percent by weight. The pH of the perm enhancer is advantageously from about 3 to about 9; the pH of the perm Enhancer is more advantageously from about 4 to about 7 in order to control the swelling of hair while perming.

Dry hair may be wrapped onto the perm-rods, preferably misting the dry hair with enhancer or wrapping dry hair as such without any enhancer or other moisture. Although the curl levels are good and similar with or without the use of enhancer, other desirable benefits are obtained when the enhancer is used for wrapping. These benefits include: (1) improved combing and detangling of hair; (2) improved control of hair and removal of static flyaways; (3) easier and more even wrapping; (4) more rapid wetting and penetration of waving lotion into hair; (5) reduced spillage of waving lotion while applying; (6) cleaner hair; (7) extra protection and conditioning to penned hair, especially for fragile hair types like bleached, frosted and overly tinted hair types; (8) infusion of hair nutrients like amino acids, proteins, moisturizers, etc., that are beneficial to the hair to be permed.

The enhancer is sparingly applied onto the dry hair evenly, just enough to create a very thin coating of product on the hair. Various methods of applications of enhancer or other moisture may be used, including misting and dropwise application. While further discussion of the application is specific to misting, the application is not so limited. After misting, the hair is combed well to remove any tangles and to spread product evenly from root to end, and then wrapped onto the perm-rod. Approximately 0.2 grams of enhancer is used for about 2 grams of hair (about 10% of the weight of the hair) that is to be wrapped onto a perm-rod. A total of about 5 to 10 grams of enhancer can be used for a full-head wrapping, depending on the length and density of hair. First, the major portion of the enhancer can be applied onto the whole head to free tangles and to spread product evenly from root to end by combing, followed by additional misting of enhancer or water as needed for wrapping hair onto each perm-rod. As much as one half of the applied enhancer may evaporate from the hair leaving only about half the amount of product staying on hair 15 minutes after wrapping. A little more enhancer can be misted onto fragile tinted and bleached hair for extra protection. Care should be taken not to overmist or saturate hair with the enhancer, which may result in weaker curls. Wrapped hair with applied enhancer may be at least partially dried prior to waving lotion application for 5 to 10 minutes under a salon dryer or using a diffuser or any other drying device to remove any excess moisture to get consistent curl results. A salon dryer may be advantageously used for even results.

Optionally, a preconditioner may be used especially for dry, coarse hair to provide extra conditioning and other beneficial hair nutrients for a healthy penned hair. The preconditioner is formulated with selected wetting, conditioning and moisturizing ingredients, which are compatible with the neutralizer. Beneficial hair nutrients like botanical extracts and amino acids may also be incorporated in the formula.

The preconditioner, if used, is delivered in a fine mist from a spray bottle. It is sparingly and evenly misted onto all the wrapped hair about 5 times to cover all the wrapped hair just before or after the creep step.

The product and processing comparisons of the conventional perms and the perms of the present invention are very important to understand and appreciate the innovative concepts of the new invention. A comparison of the methods of the present invention and the methods of the prior art, conventional perms is shown in Table 1.

TABLE 1

|   | Present Invention | Conventional Perms |
| --- | --- | --- |
| 1. (a) waving chemicals (as thioglycolic acid) in alkaline waving formulas | up to 5% by weight | up to 19% by weight |
| (b) GMT in acid perms | up to 12 grams | up to 36 grams |
| 2. Alkaline ingredients (as Ammonia) in waving formula | up to 0.5% by weight | up to 1.6% by weight |
| 3. Thio and Ammonia odor during processing | 1X | 3X |
| 4. Hydrogen Peroxide in Neutralizer | up to 1% by weight | up to 2.8% by weight |
| 5. Waving Lotion Processing Times | | |
| Normal hair | 4–6 min | 20–30 min |
| Tinted hair | 3 min | 10–20 min |
| Bleached hair | 0–3 min | 5–15 min |
| 6. Neutralizing time after application | 0 min | 5 min |
| 7. Shampooing Time | not needed except on hair having heavy build up | 1 or 2 times |
| 8. Processing Condition* | room temp process | room temp. or heat activation process |
| 9. Test Curling | not required for normal and tinted hair | usually required |
| 10. Time Saving in processing and neutralizing | 15–20 min | — |

TABLE 1-continued

| | Present Invention | Conventional Perms |
|---|---|---|
| 11. Water Saving | about 30 to 40% | — |
| 12. Spillage of Waving Lotion while applying | less than 1% | more than 30% |
| 13. Velcro Rollers for Wrapping | can be used for soft curl results | not used |
| 14. Use of Perm Enhancer | used to enhance wetting and penetration of waving lotion into hair | not used |
| 15. Curl Stabilization ("creep" step) | used to enhance good realignment of the half cystine units for effective relinking and to remove excess moisture from hair | mostly not used |
| 16.** Use of Self-heating Waving Lotion | optional | commonly used |

*Heat activation is optional and can be used with the new invention for normal and tinted hair types in order to make the processing time much shorter or to make the waving lotion much milder or to achieve tighter curl results. The new invention recommends room temperature processing for safety and comfort. Heat can cause more hair damage and possibly scalp irritation on some individuals.
**Can be used on normal and tinted hair in order to make the processing time much shorter or to make the waving lotion much more milder or to achieve tighter curl results. The new invention does not recommend this because a lot more active chemicals are used in these formulas to generate heat. Heat can cause more hair damage and possibly scalp irritation on some individuals.

The low concentrations of waving chemicals used in the method of the present invention makes it safer than prior art perm methods. In the United States, about 50% of the perms used by professional salons are acid perms. However, there has been gradual decline in the use of acid perms elsewhere, especially in Europe because of the allergic response and sensitization problems of some clients' scalp or skin caused by waving chemicals used in acid perms. Glycerylmonothioglycolate (GMT), the main waving ingredient of acid perms is responsible for the problems. Inspite of all the precautions taken to make acid perms safe, the problems still exists for some clients and hairdressers as well.

The reasons for the problems are quite apparent. GMT is not a strong waving chemical, but it perms the hair with less swelling and damage. GMT is forced to perform in the conventional acid perms in the following ways: (1) a large amount of GMT is used in conventional perms (2) a long processing time of about 20 to about 30 minutes for normal hair is not uncommon (3) heat activation is very often recommended for acid perms. Thus, the large amount of GMT, a longer processing time, which results in a longer contact time of waving lotion with the scalp, plus the heat activation, all add up to or intensify the problem and make it unsafe for many clients and hairdressers.

One of the aims of the methods of the present invention is to provide the superior perm performance while maintaining safety for clients, hairdressers, and also the environment. The present invention provides a solution in the following manner. For example, to perm untreated normal hair (1) the present invention uses about 12 grams of GMT (80% "active") in an acid perm while many conventional acid perms use up to 36 grams. Effectively, from about 1 to about 10 percent by weight of GMT is used, expressed as equivalent of thioglycolic acid. That is, conventional acid perms use about 100 to 200% more GMT than the new invention. (2) The new invention perms the hair in a very short time of up to about 5 minutes while conventional perms process for 20 to 30 minutes. That is about 300 to 500% longer than the processing time of the new invention. (3) The new invention brings out desirable results using room temperature processing while the conventional perms often recommend heat activation up to 20 to 25 minutes.

The present invention also works for alkaline perms to achieve superior and the safe perms. About 5% by weight of thioglycolic acid is used, as compared with conventional alkaline perms using up to about 19% thioglycolic acid. About 0.5% of alkaline ingredients in both alkaline and acid perm formulas is used, as compared with conventional perms using up to 1.6% alkaline ingredients. In addition, about 1.0% hydrogen peroxide in the neutralizer is used for both alkaline and acid perms, while many conventional neutralizers contain up to 2.8% hydrogen peroxide. The low concentrations of waving chemicals and the short room temperature processing makes the present method safer than prior art methods. The concentration of waving chemicals is about 66 percent lower than for conventional, prior art perms, which reduces exposure of the client, client's hair, the hairdresser, and the environment to the waving chemicals. The lower concentration of waving chemicals also decreases the amount of chemicals discharged to sewer systems.

While the method of the present invention as heretofore described has been directed to permanently waving hair, the method may generally also be applied to straighten hair. Generally, hair that has been permanently waved or naturally curly hair may be straightened using the methods of the present invention. As described herein, to straighten hair a waving lotion containing a relatively low concentration of at least one reducing agent is applied to essentially dry hair. The hair having the applied waving lotion is then combed or otherwise tensioned for up to about 10 minutes to allow sufficient bond breaking to occur, followed by neutralization. Similar benefits of essentially dry hair and low concentration of waving lotion are realized for straightening, or curl removal, as is seen for permanent waving of hair using the methods of the present invention.

EXAMPLES

The following Examples further illustrate the methods of the present invention.

Example 1

Water Absorption by Hair

Measurements were made on different hair types to determine the amount of water absorbed by hair after it was wrapped onto the rod. Untreated hair samples received from DeMeo Brothers and International Hair Importers were used for this study in the form of hair swatches each having about 2 grams of hair. The above hair samples were tinted or bleached twice using professional salon products in our lab, which were included for this study.

TABLE 2

MOISTURE PRESENT IN HAIR DURING CONVENTIONAL WRAPPING

| Hair Type | Source of Hair | % Water Absorbed |
| --- | --- | --- |
| Untreated | DeMeo & International | 65–70% of the hair weight |
| Tinted | DeMeo & International | 68–73% of the hair weight |
| Bleached | DeMeo & International | 75–81% of the hair weight |

The above percentage range covers 6 measurements on each hair type.

As shown in Table-2, the amount of water absorbed by hair is quite large, which differs according to the various sources of hair and different chemical treatments given to the hair. In reality, this percentage will be even higher when many hairdressers and home permanent users tend to wrap hair with more moisture in it.

Example 2

Dilution of Waving Lotions by Water in Saturated Hair

The dilution of waving lotions by water in saturated hair occurring during perming was calculated in the following way: the average amount of waving lotion applied to a full head of hair is about 108 grams. The number of perm-rods used per head is about 40–50. For the calculation, the amount of waving lotion applied is 2.5 grams, and the weight of dry hair before shampooing is 2.0 grams. The data from Table-2 can be used for this calculation.

TABLE 3

PERCENT DILUTION OF WAVING LOTION OCCURRING DURING CONVENTIONAL PERMING

| Hair type | % water absorbed By wrapped hair after shampooing* | Amount of water in 2 grams of wrapped hair | % Dilution of applied lotion to wrapped hair |
| --- | --- | --- | --- |
| Normal | 67.40% | 1.35 grams | 35.1% |
| Tinted | 70.47% | 1.41 grams | 36.1% |
| Bleached | 78.20% | 1.56 grams | 38.4% |

*Data from TABLE-2
Hair Source: DeMeo & International

The data in Table 3 clearly indicates that a considerable amount of dilution takes place in the applied waving lotion during conventional perming.

Example 3

Spillage of Waving Lotion

An experiment was carried out to determine the amount of spillage of waving lotion while applying to hair wrapped by both the conventional and the methods of the present invention. Hair swatches of untreated normal, tinted and bleached hair were used for this study. Six swatches of each hair type weighing exactly 2 grams of hair and tied by rubber bands were used. For conventional wrapping, 3 swatches were given a shampoo, towel-blotted and allowed to rest for 10 minutes to simulate salon-wrapping timings. They were again towel-blotted or misted with water to have the right dampness and wrapped onto a perm-rod having a diameter of about 1.15 cm, without using an end paper.

For the present invention, about 0.2 grams of "Enhancer" was misted on evenly to the dry hair of the swatch, combed well, and then wrapped onto a perm-rod of the same size, without using an end paper. The purpose of not using an end paper for wrapping was to let the waving lotion saturate the hair only, not the end paper.

The freshly wrapped swatch was then placed on a small plastic weigh-boat of known weight so that only the plastic portion of the perm-rod touches the weigh-boat, but not the hair. Exactly 2.5 grams of waving lotion was taken in a transfer pipette and applied to the wrapped hair in about half the speed of a salon application. The lotion was applied first to the top, then to the bottom, and then to the middle of the swatch evenly, repeating until all the 2.5 grams of waving lotion was applied. Then after waiting for 30 seconds, the weigh-boat containing any spilled waving lotion was weighed. The experiment was repeated and the weight of spilled waving lotion was determined for each swatch wrapped by the conventional and by the new invention method. The percentages of waving lotion spilled while applying are given in Table-4.

TABLE 4

WAVING LOTION SPILLED WHILE APPLYING

| Hair Type | New Invention | Conventional |
| --- | --- | --- |
| Normal | 0.3% | 34.0% |
| Tinted | 0.3% | 38.4% |
| Bleached | 0.3% | 38.1% |

The above percentage is the average of 3 measurements on each hair type.

The data in Table-4 indicates that about one-third of the waving lotion spills while applying during conventional perming because of the hindrance caused by the high percentage (over 65%) of water in the shampooed, damp hair, and its inability to absorb more beyond a limit. But for the New Invention, the spilling of applied waving lotion to the wrapped hair is less than 1%. This means that the applied waving lotion has the opportunity to penetrate into hair at once, almost with full strength to do the waving action. These conditions are so favorable that the best and the safest perm results can be achieved using the mildest waving products in the shortest processing times through the New Perming System of the Invention.

Example 4

Effect of Alkaline Perms on Hair Porosity

The total porosity of hair is a measure of its full capacity to absorb and hold water. Total porosity of hair provide information on the swelling and porous nature of hair. For untreated normal hair, the total porosity is in the range of 30 to 35%, and for tinted hair around 34 to 38%. When hair is permed, there is always an increase in porosity i.e. there is an increased swelling in permed hair. The increase in porosity of permed hair over the original unpermed hair provides a measure of damage caused by perming.

The percent total porosity of hair permed using conventional salon alkaline perms and the alkaline perms of the present invention were determined and compared for the hair damage.

For normal hair, a mild conventional alkaline waving lotion consisting of 8.7 percent by weight of thioglycolic acid and 0.77% ammonia at 9.38 pH was used. This is referred to herein as waving lotion A. The normal hair was processed with waving lotion A at room temperature for 20 minutes, followed by neutralization with a neutralizer containing 2.3 percent by weight of hydrogen peroxide for 5 minutes.

For tinted hair a mild conventional alkaline waving lotion consisting of 6.0 percent by weight of thioglycolic acid and 0.59 percent by weight of ammonia at 9.38 pH was used. This is referred to herein as waving lotion B. The tinted hair was processed with waving lotion B at room temperature for 15 minutes, followed by neutralization with a neutralizer containing 2.3 percent by weight of hydrogen peroxide for 5 minutes.

For the alkaline perm of the present invention, a waving lotion for both normal and tinted hair was prepared consisting of 5.0 percent by weight of thioglycolic acid and 0.46 percent by weight of ammonia at pH 9.1. This is referred to herein as waving lotion C. Normal hair was processed with waving lotion C for 5 minutes and tinted hair was processed for 3 minutes followed by 10 minutes creeping and instant neutralization with a neutralizer containing 1.0 percent by weight of hydrogen peroxide.

Total porosity of the hair samples was determined by soaking the hair in water for about one hour, centrifuging the gently blotted damp hair for 45 minutes at 3000 rpm to remove excess moisture around it using an absorbing device such as a laboratory tissue in the centrifuge tube, and finally drying the centrifuged hair in a glass weighing bottle for an hour in a vacuum oven, temperature maintained at about 105 C. to about 115 C. and the vacuum maintained at about 27" out 30" Hg. The percent total porosity was calculated as the ratio of the mass of water removed during vacuum drying to the mass of hair after vacuum drying.

The results of the total pororsity measurements for alkaline perms are given in Table 5.

The data of total porosities of permed hair in Table-5 shows that, depending on the different hair sources and hair types (normal and tinted), the increase in Total Porosity of permed hair is about 100 to 200% more for the hair permed by one of the mild conventional alkaline perm formulas than that of the new invention's alkaline perm. This means that the new invention's alkaline perm creates much less hair swelling or damage in the normal and tinted permed hair as compared to the conventional alkaline perm. The new invention is not compared against a much stronger conventional perm formulas, for example, like the exothermic or self heating formulas in order to show a big difference in hair swelling. The purpose is to dramatize how the new invention performs much gentler, creating much less hair swelling than one of the mild conventional perm formulas.

Example 5

Effect of Acid Perms on Hair Porosity

The percent total porosity of hair permed using conventional acids perms and the acids perms of the present invention were determined and compared for the hair damage.

For the conventional acid perm for normal and tinted hair, a waving lotion consisting of thioglycolic acid ester and salt at a concentration of 12 percent by weight as thioglycolic acid and 0.75% ammonia at 8.1 pH was used. This is referred to herein as waving lotion D. The normal and tinted hair was processed with waving lotion D at room temperature for 20 minutes, followed by neutralization with a neutralizer consisting of 2.3 percent by weight of hydrogen peroxide for 5 minutes.

For the acid perm of the present invention, a waving lotion for both normal and tinted hair was prepared consisting of thioglycolic acid ester and salt at a concentration of 6.3 percent by weight as thioglycolic acid and 0.42 percent

TABLE 5

COMPARISON OF TOTAL POROSITIES OF HAIR PERMED BY ALKALINE PERMS

| Hair | | % Total Porosities of Hair (1) | | | Porosity | Comparison |
|---|---|---|---|---|---|---|
| Source | Type | Conventional Perming (2) | New Invention (3) | Untreated Control | Increase | Conventional vs. New Invention |
| DeMeo | Normal | 42.61 | 37.71 | 35.05 | 7.56/2.66 | 2.84:1 |
| International | Normal | 43.65 | 37.58 | 33.11 | 10.54/4.47 | 2.36:1 |
| International | Normal | 43.48 | 37.90 | 33.11 | 10.37/4.79 | 2.16:1 |
| Single head (US) | Normal | 43.75 | 34.22 | 30.29 | 13.46/3.93 | 3.42:1 |
| International | Normal | 43.90 | 37.67 | 33.11 | 10.79/4.56 | 2.37:1 |
| International | Normal | 43.12 | 37.57 | 33.11 | 10.01/4.46 | 2.24:1 |
| Single head (European) | Normal | 42.90 | 35.52 | 32.56 | 10.34/2.96 | 3.49:1 |
| DeMeo | Tinted | 45.72 | 40.57 | 36.48 | 9.24/4.09 | 2.26:1 |
| International | Tinted | 45.83 | 39.20 | 34.01 | 11.82/5.19 | 2.28:1 |
| Single head (European) | Tinted | 49.63 | 41.86 | 37.74 | 11.89/4.12 | 2.89:1 |
| Single head (European) | Tinted | 49.57 | 41.86 | 37.74 | 11.83/4.12 | 2.87:1 |

(1) Each total porosity value is the average of 3 measurements
(2) For conventional perms, lotion A used for normal hair, lotion B used for tinted hair
(3) For present invention, lotion C used for both normal and tinted hair by weight of ammonia at pH 7.9–8.0. This is referred to herein as waving lotion E. Normal hair was processed with waving lotion E for 5 minutes and tinted hair was processed for 3 minutes followed by 10 minutes creeping and instant neutralization with a neutralizer containing 1.0 percent by weight of hydrogen peroxide.

Total porosity of the hair samples was determined as described in Example 4.

The results of the total porosity measurements for acid perms are given in Table 6.

when the hair is (1) processed optimally without any over or under-processing (2) neutralized completely (3) free of any waving chemical trapped inside hair (4) processed evenly from root to end (5) given the best realignment of the half-cystine units for the most efficient relinking of bonds (6) permed with the least swelling in hair (7) neutralized with the least amount of cysteic acid formed inside hair due to over-oxidation The measurement of curl relaxation was carried out on hair swatches permed similar to Example 4 with lotions A, B, and C. About a one-eighth portion of the hair staying on,

TABLE 6

COMPARISON OF TOTAL POROSITIES OF HAIR PERMED BY ACID PERMS

| | | % Total Porosities of Hair (1) | | | | Comparison |
|---|---|---|---|---|---|---|
| Hair Source | Type | Conventional Perming (2) | New Invention (3) | Untreated Control | Porosity Increase | Conventional vs. New Invention |
| DeMeo | Normal | 39.26 | 35.79 | 35.05 | 4.21/0.74 | 5.69:1 |
| International | Normal | 40.50 | 35.62 | 33.11 | 7.39/2.51 | 2.94:1 |
| International | Normal | 40.27 | 35.86 | 33.11 | 7.16/2.95 | 2.60:1 |
| International | Normal | 40.49 | 35.68 | 33.11 | 7.38/2.57 | 2.87:1 |
| International | Normal | 39.23 | 35.58 | 33.11 | 6.12/2.47 | 2.48:1 |
| Single head (US) | Normal | 39.60 | 33.70 | 30.29 | 9.31/3.41 | 2.73:1 |
| Single head (European) | Normal | 38.56 | 34.06 | 32.56 | 6.00/1.50 | 4.00:1 |
| DeMeo | Tinted | 43.62 | 38.12 | 36.48 | 7.14/1.64 | 4.35:1 |
| International | Tinted | 43.41 | 37.05 | 34.01 | 9.40/3.04 | 3.09:1 |
| Single head (European) | Tinted | 47.62 | 40.80 | 37.74 | 9.88/3.06 | 3.23:1 |
| Single head (European) | Tinted | 47.57 | 40.80 | 37.74 | 9.83/3.06 | 3.21:1 |

(1) Each total porosity value is the average of 3 measurements.
(2) For conventional perms, lotion D was used for both normal and tinted hair
(3) For present invention, lotion E was used for both normal and tinted hair The data of total porosities of permed hair in Table 6 shows that, depending on the different hair sources and hair types (normal and tinted), the increase in Total Porosity of permed hair is about 100 to 300% more for the hair permed by conventional acid perm formula than that of the new invention's acid perm. This means that the new invention's acid perm creates much less hair swelling or damage in the permed hair as compared to the conventional acid perm that processes at room temperature.

Example 6

Curl Relaxation of Hair Permed by Alkaline Perm

The curl relaxation or conversely the curl longevity study is important for permed hair. Long lasting curls are achieved in the middle of the swatch was used for the study. The curl lengths of swatches understudy were determined in both wet and dry stages prior to shampooing. The swatches were grouped together with a rubber band, shampooed for a minute, rinsed well with warm water for a minute, towel-blotted, and then dried well using a blowdryer at medium setting. This procedure was repeated 9 more times. After the $10^{th}$ shampoo, a light rinse-off conditioning treatment was given to avoid hard combing, dragging, or too much stretching of the curls. The curl lengths were determined for both wet and dry stages after 10 shampoos. The percent Curl Relaxation was calculated from the above two curl lengths and the length of the original straight hair prior to perming. Shampooing, rinsing with warm water, and blow-drying generally relax the permed curls gradually. This study was done at least one day after perming the hair.

TABLE 7

CURL RELAXATION OF PERMED HAIR AFTER 10 SHAMPOOS

| Hair | | % Curl Relaxation of Hair Permed by | | | | Comparison | |
| --- | --- | --- | --- | --- | --- | --- | --- |
| | | Conventional Alkaline Perms (1) | | New Invention's Alkaline Perm (2) | | Conventional vs. New Invention | |
| Source | Type | WET Stage | DRY Stage | WET Stage | DRY Stage | WET Stage | DRY Stage |
| International | Normal | 25.0 | 26.0 | 3.4 | 4.0 | 7.4:1 | 6.5:1 |
| International | Tinted | 24.3 | 26.7 | 5.8 | 3.9 | 4.2:1 | 6.8:1 |
| International | Normal | 28.0 | 32.0 | 3.4 | 4.0 | 8.2:1 | 8.0:1 |
| International | Tinted | 29.1 | 32.1 | 5.8 | 3.9 | 5.0:1 | 8.2:1 |
| International | Normal | 21.1 | 23.2 | 3.0 | 3.4 | 7.0:1 | 6.8:1 |
| DeMeo | Normal | 17.1 | 15.4 | 3.9 | 4.5 | 4.4:1 | 3.4:1 |
| DeMeo | Tinted | 14.8 | 17.4 | 4.0 | 4.5 | 3.7:1 | 3.9:1 |
| DeMeo | Normal | 26.0 | 26.4 | 6.3 | 3.9 | 4.1:1 | 6.8:1 |
| Single head (European) | Normal | 20.0 | 19.4 | 4.0 | 4.5 | 5.0:1 | 4.3:1 |
| Single head (European) | Tinted | 23.3 | 24.4 | 7.7 | 7.7 | 3.0:1 | 3.2:1 |

(1) lotion A for normal hair, lotion B for tinted hair
(2) lotion C for normal and tinted hair The data on Percent Curl Relaxation of permed hair in Table 7 shows that, depending on the different hair sources and hair types (normal and tinted), the curl relaxation of permed hair is about 200 to 600% more for hair that is permed by the conventional salon alkaline perm formulas than that of the new invention's alkaline perm. This means that the curls of the new invention are about 200 to 600% more lasting than the curls of the conventional salon alkaline perms.

Example 7

Curl Relaxation of Hair Permed by Acid Perm

The measurement of curl relaxation was carried out on hair swatches permed similar to Example 5 with lotions D and E. All other conditions were similar to those described in Example 6. The results are shown in Table 8.

TABLE 8

CURL RELAXATION OF PERMED HAIR AFTER 10 SHAMPOOS

| Hair | | % Curl Relaxation of Hair Permed by | | | | Comparison | |
| --- | --- | --- | --- | --- | --- | --- | --- |
| | | Conventional Acid Perms (1) | | New Invention's Acid Perm (2) | | Conventional vs. New Invention | |
| Source | Type | WET Stage | DRY Stage | WET Stage | DRY Stage | WET Stage | DRY Stage |
| International | Normal | 24.3 | 24.0 | 6.3 | 7.1 | 3.9:1 | 3.4:1 |
| International | Tinted | 24.9 | 26.7 | 6.3 | 7.1 | 4.0:1 | 3.8:1 |
| International | Normal | 20.5 | 16.8 | 3.0 | 3.4 | 6.8:1 | 4.9:1 |
| DeMeo | Normal | 15.4 | 16.7 | 7.1 | 8.3 | 2.2:1 | 2.0:1 |
| DeMeo | Tinted | 18.6 | 17.4 | 3.9 | 4.0 | 4.8:1 | 4.4:1 |
| DeMeo | Normal | 28.6 | 33.3 | 9.5 | 3.9 | 3.0:1 | 8.5:1 |
| Single head (European) | Normal | 20.0 | 18.6 | 3.3 | 4.0 | 6.1:1 | 4.7:1 |
| Single head (European) | Tinted | 27.9 | 30.6 | 7.7 | 9.0 | 3.6:1 | 3.4:1 |
| Single head (European) | Tinted | 26.8 | 30.6 | 7.7 | 9.0 | 3.5:1 | 3.4:1 |

(1) lotion D
(2) lotion E

The data on Percent Curl Relaxation of permed hair in Table 8 shows that, depending on the different hair sources and hair types (normal and tinted), the curl relaxation of permed hair is about 100 to 500% more for hair that is permed by the conventional salon acid perm than that of the present invention's acid perm. This means that the curls of the present invention are about 100 to 500% more lasting than the curls of the conventional salon acid perms.

Example 8

Penetration of Wave Lotion into Hair

An experiment was carried out to determine the percentage of applied waving lotion that penetrates into wrapped hair within the lotion application time of 3 minutes. It takes about 3 to 5 minutes for the hairdresser to apply the waving product to a full head of hair that is wrapped onto about 40 to 50 perm-rods. The application time depends on the number of perm-rods used for a client. A comparative study was done on normal, tinted and bleached hair types. Exactly, 1.98 to 2.02 grams of 7-inch long hair was tied with a rubber band and used as a swatch.

Three untreated-normal swatches were wrapped according to the new invention, misting about 0.2 grams of perm Enhancer to the dry hair of a swatch and one wrapped onto a small-size perm-rod (diameter of 0.99 cm), the second one to a medium-size perm-rod (diameter of 1.15 cm), and the third one to a large perm-rod (diameter of 1.46 cm) without using an end-paper.

Three untreated-normal swatches were wrapped according to the conventional way. All these swatches were shampooed once, towel-blotted enough to have the right dampness and then wrapped onto perm-rods similar to the one used for the new invention, without the use of end papers. Exactly 2.0 grams of a waving lotion was slowly applied from a pipet to the wrapped swatch kept in a plastic weigh boat, first to the top, after about 1 minute to the bottom, and again after another minute, to the top, bottom and sides. At the end of the 3-minute lotion application time, the swatch was carefully taken out of the perm-rod, collecting all the dripping lotion into a 250-ml glass beaker. Then the excess lotion from the swatch was squeezed out gently and uniformly thrice, collected into the same beaker. Removing of the swatch from the rod and squeezing of lotion etc. takes about 1 minute. The spilled lotion, if any, was also completely transferred from the weigh-boat into the beaker. The collected lotion, which did not penetrate into hair within the 3-minute application time was then titrated with 0.1 N HCl to determine the alkaline content, that is, the ml equivalent of 0.1 N HCl ("b"). The ml equivalent of 0.1 N HCl ("a") also was determined for 2 grams of waving lotion used. The approximate amount of waving lotion that penetrated into hair within 3–4 minutes of the application time was calculated:

% waving lotion penetrated into hair=$(a-b)/a \times 100$.

This experiment was repeated for each swatch, and the average of 3 measurements for each hair type such as normal, tinted, and bleached hair was determined. It was noticed that the results were close for each hair type irrespective of the different size perm-rods used for both the new invention and the conventional way of wrapping.

TABLE 9

PENETRATION OF WAVING LOTION INTO HAIR WITHIN THE PRODUCT APPLICATION TIME

| Hair Type | Perming by New Invention | Conventional Perming |
| --- | --- | --- |
| Normal | 94.1% | 73.4% |
| Tinted | 94.9% | 75.5% |
| Bleached | 99.1% | 77.2% |

The above results are the average of 3 measurements.

The data in Table 9 shows that the amount of waving lotion penetrating into hair within the application time is at least 20% more for the new invention than that of the conventional method of perming. The data also indicates that using the method of the present invention, more than 94% of the waving lotion applied penetrates into normal or tinted hair, and about 99% penetrates into bleached hair within the 3-minute application time. This means that using the methods of the present invention, almost all the applied waving lotion penetrates quickly into the wound essentially dry hair and starts the waving action almost with full strength immediately.

Example 9

Color Retention During Perming of Tinted Hair

Natural white hair from International Importers was tinted twice with permanent and semipermanent colors. Tinted white hair was used for the colorlift study because any color loss can be easily noticed on white hair. Colorlift after perming was observed also on dark or light brown hair from DeMeo Bros. and International Importers, which were tinted twice in the lab. These tinted swatches were permed similarly by the same alkaline and acid perms of the new invention and also the alkaline and acid conventional perms used in Examples 4 and 5 to study the colorlift.

It was noticed that much more color is lifted by the conventional alkaline and acid perms than the alkaline and acid perms of the new invention. It was also noticed that the perm Enhancer of the invention gives extra protection for the color of tinted hair. The color stays on better when the perm Enhancer is used for wrapping hair than not using it. The reason is quite obvious that the mildest waving products and the shortest processing times of the new invention and also the use of perm Enhancer for wrapping work gently on the color of tinted hair. The cumulative effect of the above mentioned reasons protect the color of tinted hair and make the new invention the ideal choice for perming tinted hair types.

Example 10

Curl Removal Treatment for Permed Curly Hair and Naturally Curly Hair

A set of three identical curly hair swatches was used for each study. For conventional treatment, one hair swatch was given a shampoo, towel-blotted well, and combed to free tangles. For the new invention method, perm Enhancer was sparingly and evenly misted onto one dry swatch, and combed well. The third swatch was not given any treatment. A mild waving lotion having 5% by weight thioglycolic acid, 0.46% ammonia and a pH of 9.1 was applied to the curly hair and combed intermittently using uniform tension. After a specified time, all the swatches were rinsed well, towel-blotted, and neutralized for 5 minutes using a neutralizer containing 1% by weight of hydrogen peroxide. Curl lengths were measured for all hair swatches before and after treatment for calculation. The Percent Curl Removal is given in Table-10.

TABLE 10

PERCENT CURL REMOVAL ON CURLY HAIR

|  | Conventional | New Invention |
|---|---|---|
| *% curl removal for normal permed hair | 80.0% | 97.2% |
| **% curl removal for tinted permed hair | 81.0% | 97.0% |
| ***% curl removal for naturally curly hair | 12.7% | 29.3% |

Treatment times:
*5 minutes;
**3 minutes;
*** 10 minutes

The curl removal is better for the new invention again because of the obvious reasons that waving lotion penetration is quick and least dilution occurs to the waving lotion.

Example 11

Curl Results

A mild alkaline waving lotion of the invention having 5.0% by weight of thioglycolic acid, 0.46% by weight of ammonia, and a pH of 9.1 was used to perm 8-inch-long untreated normal and tinted hair swatches (from International Importers) and 7-inch-long bleached hair swatches (form DeMeo Bros.). Neutralizer having 1% by weight of hydrogen peroxide was used for instant neutralization. The perm Enhancer was used to wrap each dry swatch, misting about 0.2 grams per swatch. Perm-rods of different sizes, the smallest having a diameter of 0.67 cm and the largest one having a diameter of 1.46 cm were used. Different types like concave and straight perm-rods were also used. A total of 17 hair swatches were perrned by the New Perming System of the invention.

All normal and tinted swatches were permed at room temperature with a processing cap. The bleached hair swatches were rinsed right after the 3-minute application time. That is, the bleached hair was given a 0-minute processing time. Normal hair was processed for 5 minutes and tinted hair for 3 minutes. After rinsing and towel-blotting, all the swatches were creeped for 10 minutes without a cap under salon dryer at medium setting (54–56° C.). After the creep, all the swatches were neutralized giving 0-minute neutralizing time.

Very good curls with excellent spring and condition were achieved for each hair type and for each perm-rod through the New Perming System of the invention. Great curls are achieved by the concepts and techniques of the new invention: (1) using very mild waving lotion that is mild enough to perm bleached hair (2) very short processing times of 5 minutes for normal hair, 3 minutes for tinted hair, 0 minutes for bleached hair are capable of creating great curls through the new invention (3) uniform curl results, even on very small perm-rods proves that the distribution of waving lotion is uniform from root to end of the 8-inch long wrapped hair because the waving lotion can thoroughly and quickly penetrate to the ends with least hindrance (4) the Enhancer of the invention helps wrapping, quick wetting and penetration of waving lotion into hair and also gives protection to hair, especially for fragile hair types like bleached and tinted hair to give very good curls without any overprocessing and least colorlift from the tinted hair (5) application of waving lotion to wrapped hair that is almost dry helps quick penetration with least spillage (6) a very mild waving lotion giving very good curl on a strong normal hair in a very short time means that the applied lotion penetrates quickly to do the waving action without spillage or getting diluted by any saturating water (7) 1 0-minute creep is very beneficial to provide very good realignment of half-cystine units and also to remove an optimum amount of moisture from processed damp hair to make instant neutralization very effective (8) very mild neutralizer having 1.0% by weight of hydrogen peroxide is very effective in providing instant neutralization (9) a zero-processing time for bleached hair also indicates quick penetration of waving lotion and immediate waving action as revealed by the new invention to give very good curls in the shortest time.

DISCUSSION

The new invention opens the door to a new era in ideal perming with multitudes of great benefits. The new invention makes the perming very simple, safe, quick and easy to perform and understand. The new invention will remove the fear and hesitation out of a great number of people throughout the world and thereby will boost the global perm market.

Superior performance and utmost safety for the perm clients, hairdressers and the environment are the highlights of the new Invention.

Better perm results than the conventional perming will be achieved through the new Invention by using (1) 50 to 75% lesser amounts of reactive chemicals in the waving lotion and neutralizer (2) much reduced levels of alkaline ingredients in waving lotion (3) very short processing times that are not only about one-fourth of timings given for the conventional perming, but also can be processed instantly using a zero-processing time. The benefits of the new invention are the cumulative effect of the new perming concepts, the ultra mildness of the waving products, and the very short processing timings.

A good number of people have sensitive scalps and skin who develop redness, itching or some other allergic reactions when they get a perm. Lots of people are reluctant to get a perm because of the fear of such reactions. Though the allergic reactions generally go away after a while, they still pose a big problem. The strong odor of waving chemicals and tearing due to ammonia are the other minor problems due to high-strength conventional formulations. The new Invention will greatly minimize or virtually eliminate such reactions, minimize strong odor, tearing, etc., and take away the fear and hesitation out of such sensitive clients. This benefit is apparently the outcome of perming with ultra mild waving lotion containing only small amounts of odorous waving chemicals and ammonia, and also due to very safe room temperature processing and very short processing times used by the new invention.

A client spends about two hours in the salon or at home to get a perm, twice or thrice a year. But the hairdresser spends many more hours each day, up to six days a week smelling and working with waving and other products. The new invention provides safety and comfort for the hairdresser again through the ultra mildness of the waving products and good time savings by the short processing times of 0 to 5 minutes. There will be a boom in business for hairdressers when perming becomes an enjoyable treat.

The hair damages and overprocessings that occur during perming depends on many factors like the levels of active chemicals, pH of formulations, heat activation, the duration of the processing, the contact time of waving products with hair, and the condition of the processing, that is, processing at room temperature or under dryer-heat. The new invention offers the following most favorable conditions for the least damage: (1) about 50 to 75% reduced waving chemicals and alkaline materials (2) low pH (3) very short processing times (4) room temperature processing without the use of heat (5) if dryer-heat or a self-heating waving lotion is used, a much gentler lotion and/or much shorter processing times will be recommended to compensate for the heat activation so that hair is permed with least damage at all times. Thus, the new invention minimizes hair damage and leaves the hair almost intact with natural feel, look, and elasticity. Besides safeguarding the hair, the invention also is gentle on the color of tinted hair, again through the ultra gentleness of waving products and short processing times.

The "no wait" neutralizing or the instant neutralizing, coupled with the very gentle neutralizer (having only 1% hydrogen peroxide) minimizes the formation of cysteic acid. This is very beneficial to the safety of hair. On the contrary, the regular-strength conventional neutralizer containing up to 2.8% hydrogen peroxide and neutralizing or oxidizing for 5 minutes has its own drawbacks. The high amount of peroxide in the conventional neutralizer has a tendency to gently bleach or lighten the natural color of untreated hair, and form considerable amount of cysteic acid by converting cystine, into cysteic acid. Once the cysteic acid is formed, it never reverts back into the natural cystine, which is so essential for the strength and integrity of hair. This irreversible formation of cysteic acid occurs by over oxidation of cystine. The extent of cysteic acid formation depends on the strength and pH of the neutralizer and the duration of neutralizing, that is the contact time of peroxide of the neutralizer with hair. This situation leads to a decreased number of cystine molecules now binding the polypeptide chains inside the cortex of hair, leading to a decrease in the tensile strength and an increase in swelling tendency of penned hair. Likewise, the outer cuticle is also damaged by the peroxide, which in turn affects the natural look, shine, feel, and hydrophobicity of the penned hair. In addition, the electric charge on the permed hair increases and tends to be more negative and undesirable. The new invention controls or minimizes all the above mentioned hair damages while perming, and thus provides maximum safety for the permed hair through its ultra mild neutralizer and instant neutralizing technique.

The new invention uses about 50 to 75% less chemicals to perm hair than the conventional way of perming. This means that 50 to 75% fewer chemicals will get into the sewer, and likewise gases like ammonia and hydrogen sulfide will get into the atmosphere. Presently the laws and regulations are increasing or getting tougher throughout the world to protect and preserve the environment. It is a great concern for everyone. The new invention has come up with the right solution to control that part of the pollution problem that arises through perming chemicals.

The new invention is the right choice for the future permanent wave industry because it provides safety for the environment, manufacturers, perm clients, hairdressers and the hair that is permed.

Various benefits of the use of the methods of the present invention may be identified, including:

(i) The cost of active raw materials like ammonium thioglycolate, ammonia, hydrogen peroxide, etc., used in the ultra mild perm formulations of the new invention will be reduced by about 50 to 75% compared to that of the conventional high-strength perm formulations. It is not only cost-saving but also low inventory or a reduced storage area for the manufacturer.

(ii) The new invention's ultra mildness of waving products and short processing times will control hair damage and any possibility of overprocessing of hair during perming. Thus, it will eliminate or minimize the use of Diammoniumdithiodiglycolate (Dithio), the "stop action" ingredient which is a sulfur compound that is used in most of the perm formulations to control over-processing. No need of "Dithio" means another big cost-saving for the manufacturer and also eliminates or minimizes another sulfur compound getting into the sewer.

(iii) Likewise, the new invention will proportionately reduce the percent levels of protecting, conditioning, buffering, fragrancing and moisturizing ingredients which are used in the ultra mild perming products, to cut cost and to minimize chemicals getting into the sewer.

Mildness of the perming products with the least odor, ammonia gas and aggressiveness is a sure benefit for the compounders and people working in the filling lines. It provides more safety and comfort in the compounding and filling areas also.

A variety of combinations of formulations using very active perming ingredients like thioglycolates and thiolactates, very gentle perming ingredients like cysteine and its derivatives, cysteamine and its derivatives or a combination of the above ingredients can be made to work very efficiently at very low percentage levels, which otherwise will not be that effective in the conventional way of perming. The new invention will enable even the very gentle natural waving ingredients like cysteine to perform efficiently. Thus the new invention will initiate development of a new series of innovative ultra mild perm formulations to achieve ideal perm results.

The induced absorption and thorough penetration of waving products into the wound hair as described herein provide firmer, longer lasting, and even curls from root to end.

The method of the present invention provides enhanced neutralization in a very short time through the curl stabilizing step. Complete neutralization assures desirable curl results, lasting curls and no odor in hair after the perm. The chances of cysteic acid formation also will be reduced by the instant neutralization, and thereby the swelling tendency and weakening of permed hair also will be reduced when better realignment and rebonding occur during perming.

The combination of a thorough rinsing of waving lotion and very low levels of active chemicals in waving lotion minimizes the chances for entrapment of waving chemicals in permed hair. The chemical-free state of permed hair eliminates many undesirable negatives like mixed disulfide formation, premature curl relaxation and post-perm odor in hair.

The new invention reduces cuticular damages occurring during both the processing and neutralizing steps to assure continued protection given by cuticles, natural smooth feel and sheen for permed hair. During conventional perming, cuticular damage can take place by the following mechanism: When the strong waving lotion is applied to the wound hair, it takes time for the waving lotion to penetrate into the hair because the wrapped hair is already saturated with water which resists penetration of the waving lotion. Thus, the strong waving lotion having high amounts of waving chemicals and alkaline ingredients has a chance to attack the outer cuticles while waiting to penetrate into hair. The cuticles may crack, erupt, or loosen up depending on the aggressiveness of the waving lotion and the duration of the attack.

The type of cuticle damage occurring during conventional neutralizing, due to delayed penetration of the neutralizer into the processed hair is different from the damage caused by delayed penetration of the waving lotion. But the mechanism is about the same. The strong neutralizer, which stays around the cuticle for an extra 5 minutes, begins to lighten the color of hair due to the slow bleaching tendency of the peroxide in the neutralizer.

While not wishing to be bound by any particular theory, it is hypothersized that the reduction in cuticular damage by the methods of the present invention as compared by that which occurs during the conventional perming by the following mechanism:

(1) As required by the new invention, the wound hair being almost dry, absorbs the applied mild waving products quickly to do the perming without much delay in penetration.
(2) The ultra-mild waving products of the new invention is put into action immediately inside of hair, but not that much outside to react with cuticles.
(3) As highlighted by the new invention, the short processing or contact timing of the waving products with hair which are being reduced to about one fourth of the timings used for conventional perming, also strongly compliments our least cuticle damage claim.
(4) The Perm Enhancer of the new invention helps wetting of waving products for quick penetration. In addition to that, it also acts like a shield to provide good protection for the cuticles during the application of waving products to minimize any damage to the cuticles.

The new Invention empowers each perming chemical to perform most efficiently by itself or in a combination with others. It also enables a variety of perming chemicals, which are not in abundant use for the reasons of high cost or under restriction for use due to sensitization or allergic reactions or ineffectiveness, to perform reasonably well with least problems. Some of the commonly used problematic chemicals are discussed below.

(1) Glyceryl Monothioglycolate (GMT): GMT is used in acid perms. Acid perms generally leave the hair with less damage and swelling because of its gentle waving action and the lower pH. GMT is loosing grounds in many countries, mainly in Europe and Far East due to the sensitization and other allergic problems experienced by clients and hairdressers as well.

The new Invention provides a solution to the conventional Acid perm problems. As recommended by the new invention, the amount of GMT in the acid perm formulations can be reduced by 50 to 75% as compared to the conventional acid perms, and made to work very safely and efficiently. Also the very short, room temperature processing with least spillage or contact with scalp and skin will provide additional safety.

(2) The naturally occurring Cysteine and its derivatives like Cysteine Hydrochloride and N-Acetyl Cysteine are not that effective in perming and they are very, very expensive. Although Cysteines are good for safety reasons, their level of use in an "all natural cysteine" perm formula makes it unpractical in terms of cost and performance. The new invention which is based on lower percent actives should be cost effective and provide decent curl results, using only such a mild and natural cysteine or its derivatives which otherwise will not be possible with the conventional way of perming.
(3) Cysteamine Hydrochloride is another ingredient that is used in perming. Cysteamine also is very expensive and has an objectionable odor. It smells bad during processing and the permed hair also smells bad for a long time. Again the new invention with 50 to 75% reduced cysteamine hydrochloride in formulations will give the desired curl results with much less odor and lower cost than the conventional formulations.

Thus, the new invention makes the mild waving ingredients to perform better individually or in combination with other waving ingredients, and enables the expensive natural waving ingredients to deliver the desired curl results individually or in combination with other waving ingredients at a much lower percent level and cost than the conventional formulations. The added benefits are extra safety, minimal odor, least damage, and longer lasting healthy curls.

Firmer and tighter curls can be achieved on strong untreated normal hair types within a very short processing time of 0 to 4 minutes. Our new Invention is able to achieve this using a stronger waving lotion, yet milder than many of the strongest conventional perms on the market.

A zero-processing time means that after the full-head application of waving lotion, there is no need for any additional processing time. The wrapped hair can be thoroughly rinsed right away to remove all the waving chemicals from the hair. Conventional perms need about 20 minutes of processing time to achieve similar curl results on strong normal hair.

The New Perming System utilizes its concept of instant penetration and immediate waving action of the waving lotion inside hair when it is applied to wound hair that is almost dry or completely dry. Thus, the application time of 3 to 5 minutes is good enough for the new invention to produce excellent medium curls in the shortest zero-processing time or tighter curls within 2 to 4 additional minutes of processing, using a stronger waving lotion. Higher the strength of the waving lotion, much shorter will be the processing time.

A zero-processing time not only saves time for both the client and hairdresser, but it is also a big safety benefit for the client. The scalp-contact time of the waving product is so short that it could virtually eliminate or minimize problems of scalp sensitization, irritation, odor, tearing, etc. that are commonly associated with conventional perming. Likewise, heat activated milder waving lotions also can be made to produce medium to strong curls within a very short time of 0 to 4 minutes of processing time.

The new invention creates even curls not only from root to end but also throughout each section of the wrapped hair. When the moist hair is wrapped onto the perm-rod by conventional method, hair having an average length of eight inches and a weight of about two grams can go over the perm-rod about four to eight times, depending on the size of the perm-rod. When an inch and a half-wide section of hair is wrapped onto a perm-rod, there are portions in the wrapped hair that are favorable to get saturated with the waving products during the application of products. The edge portions of the section have the best chance to get saturated faster because product can penetrate from the top and also from the sides. But, the middle portion gets product mostly from the top but not as much from the sides. So there will be some delay in product penetration in the middle of that section of wrapped hair.

Thus for the conventional waving, the time of product penetration to the ends of wrapped hair and also the amount of product and its strength reaching the ends of wrapped hair will vary within the same section of the wrapped hair. This kind of variation introduces some differences in waving action within the same section of the wrapped hair.

A similar situation occurs during the neutralizing step also. The net result leads to a tighter curl at the edges and a slightly softer curl in the middle of each section of wrapped hair. Thus, uneven curl-results occur in conventional perming.

The present invention removes this kind of uneven curls resulting in conventional perming by recommending application of waving product to dry or almost dry hair enabling penetration of waving product from root to end throughout each section very quickly and evenly without much restriction or decrease in strength. This means, uniform perming action throughout the wrapped hair producing even curls in each section of the hair.

A comparative alkaline and acid wave permings were carried out on hair swatches that were eight inches long, about an inch and a half in width, and weighing about two grams per swatch. The results of perming by the new Perming System were compared to conventional perming for eveness of curls and curl relaxation after 10 shampoos. The New Perming System resulted in very uniform curls throughout the hair swatch while the swatches permed using conventional products and procedures gave uneven curls, which were tighter on both edges of the swatch than the middle.

The percent curl relaxation after 10 shampoos was considerable for hair permed using conventional perms. In addition, the middle portion of the curl achieved by conventional perming relaxes slightly more than the edges of the same swatch. This indicates more incomplete neutralization in the middle portion of the swatch than in the edges. Again, the delayed penetration and slow action of neutralizer is responsible for this. It also proves why it is hard to achieve even and lasting curl through conventional perming, when there is water saturated in and around hair while applying the perming products.

The even curls achieved by the innovative perming system of the new invention relax only slightly and evenly at the edges and in the middle of the swatch, indicating even penetration of waving products and complete neutralization throughout the swatch. These results provide great evidence for the concept of the new invention.

For the best curl results, the right amount of waving lotion has to go inside of hair to enable the forward reducing action to proceed to a desirable level within a specified processing time to provide enough bond breaking for the best and lasting curl results. Likewise, similar amount of neutralizer will also be needed for thorough neutralization.

The data herein indicate that a quick and even penetration from root to end of hair occurs within one minute of the application of waving lotion to hair swatches each containing eight inches long and about two grams of hair which is wrapped onto a perm rod according to the methods of the present invention. Also, quick and even penetration occurs throughout when 1.0 or 1.5 or 2.0 grams of waving lotion is applied to the wrapped hair swatches, when the hair is almost dry. Desirable results were obtained when 2.0 grams of waving lotion was applied to the hair swatch containing two grams of hair.

The amount of waving lotion needed to obtain desirable curl generally should be about equal to the weight amount of hair. This amount will also depend on the hair texture like fine, thick and porous, etc., hair length and density ranging from 1 to 3 grams per rod. Thus, the right amount of waving lotion and the concept of the new invention will provide desirable even and long lasting curls, control spillage, and provide utmost safety for clients.

What is claimed is:

1. A method of permanently waving hair, comprising the steps of:

initiating said method of permanently waving hair by taking a body of hair, having an inherent moisture content of about 10% by weight;

applying a light mist of enhancer solution to the surface of said body of hair to facilitate subsequent wrapping of said hair without appreciably increasing the moisture content of said body of hair, said misted hair being essentially dry hair and containing no more than 20% water by weight;

wrapping said body of hair onto a plurality of wrapping devices;

applying a waving lotion to said essentially dry hair prior to the application of any further external moisture;

processing the hair having the applied waving lotion to obtain permanently waved hair; and said method of permanently waving hair capable of application at all pH's with a pH range of 6.5 to 9.5.

2. The method of claim 1, wherein said essentially dry hair includes up to about 10 percent by weight moisture.

3. The method of claim 1, wherein said enhancer solution further comprises water and at least one additive selected from the group consisting of anionic, cationic, nonionic, or amphoteric surfactants, naturally derived or synthetic anionic, cationic or nonionic polymers, amino acids, botanical extracts, proteins from vegetable or animal sources, conditioning, moisturizing and chelating agents.

4. The method of claim 3, wherein the total concentration of said at least one additive is in a range of about 0.1 to about 5 percent by weight.

5. The method of claim 3, wherein the pH of said enhancer solution is from about 3 to about 9.

6. The method of claim 3, wherein the pH of said enhancer solution is from about 4 to about 7.

7. The method of claim 1, wherein said waving lotion comprises at least one reducing agent.

8. The method of claim 7, wherein said at least one reducing agent has a concentration in said waving lotion of from about 1 to about 12 percent by weight as thioglycolic acid.

9. The method of claim 7, wherein said at least one reducing agent has a concentration in said waving lotion of from about 1 to about 8 percent by weight as thioglycolic acid.

10. The method of claim 1, wherein said waving lotion comprises at least one reducing agent selected from the group consisting of thioglycolic or thiolactic acids and their derivative salts and esters, cysteine and its derivatives, cysteamine and its derivatives, inorganic sulfites and bisulfites.

11. The method of claim 1, wherein processing the hair further comprises the steps of:

rinsing the hair with water;

blotting the hair with a towel; and creeping the hair.

12. The method of claim 11, wherein the step of processing the hair includes the step of:

neutralizing the hair with a neutralizer.

13. The method of claim 12, wherein said neutralizer comprises an oxidizing agent.

14. The method of claim 12, wherein said neutralizer comprises an oxidizing agent selected from the group consisting of hydrogen peroxide, sodium bromate, potassium bromate, and sodium perborate.

15. The method of claim 12, wherein said neutralizer comprises hydrogen peroxide having a concentration in said neutralizer of from about 0.5 to about 3 percent by weight.

16. The method of claim 12, wherein said neutralizer comprises hydrogen peroxide having a concentration in said neutralizer of from about 0.8 to about 1.2 percent by weight.

17. The method of claim 11, wherein a preconditioning solution is applied to said hair before, after, or before and after said creep step.

18. The method of claim 12, wherein said neutralizing step includes application of neutralizer and a waiting time for neutralizing, said waiting time being essentially zero minutes.

19. The method of claim 11, wherein said creeping step includes exposing said hair to heated air, radiant heat, or other moisture reducing device for from about 5 minutes to about 60 minutes.

20. The method of claim 11, wherein said creeping step includes exposing said hair to heated air at a temperature of about 50 to about 60° C. for about 5 to about 15 minutes, wherein said hair is not covered with a cap.

21. The method of claim 11, wherein during said creeping of said hair the moisture content of said hair is reduced by about 20 percent to about 80 percent.

22. The method of claim 21, wherein said creep step is carried out without a cap on said hair.

23. The method of claim 11, wherein during said creeping of said hair the moisture content of said hair is reduced by from about 30 percent to about 50 percent.

24. The method of claim 11, wherein said creep step is carried out without a cap on said hair.

25. The method of claim 11, wherein during said creep step, said hair is exposed to heated air at a temperature of about 50 to about 60° C. or to radiant heat for up to about 60 minutes and said hair is covered with a cap, and wherein after said creep step said hair is not neutralized.

26. The method of claim 1, wherein said waving lotion is a waving lotion suitable for perms selected from the group consisting of acid perms, alkaline perms, perms having netural pH, or perms using buffered alkaline waving lotions.

27. The method of claim 26, wherein said waving lotion suitable for acid perms contains GMT in a concentration of from about 1 to about 10 percent by weight as thioglycolic acid.

28. The method of claim 1, wherein said wrapping devices are selected from the group consisting of perm rods, Velcro rollers, and plastic nets.

29. The method of claim 1, wherein the waving lotion includes at least one alkaline ingredient selected from the group consisting of ammonium hydroxide, sodium hydroxide, monoethanolamine, borax, ammonium carbonate, and ammonium bicarbonate.

30. The method of claim 29, wherein the total alkaline content in said waving lotion is from about 0.02 to about 1.0 percent by weight as ammonia.

31. The method of claim 29, wherein the total alkaline content in said waving lotion is from about 0.02 to about 0.7 percent by weight as ammonia.

32. The method of claim 1, wherein said essentially dry hair is shampooed and dried to an inherent moisture content of no more than about 10% prior to said wrapping and application of said waving lotion.

33. The method of claim 1, further comprising the steps of:

rinsing the hair with water;

blotting the hair with a towel; and neutralizing the hair with a neutralizer.

34. The method of claim 1, wherein said waving lotion includes at least one additive selected from the group consisting of chelating agents, cleansing herbs, anionic, amphoteric, or nonionic surfactants, anionic, cationic, or nonionic polymers, buffering agents, proteins, botanical extracts, amino acids and fragrances.

35. The method of claim 1, wherein said body of hair is returned to essentially dry condition prior to the application of said waving lotion.

36. The method of claim 1, wherein absorption of said waving lotion into said essentially dry hair is greater than 90% when an approximately equal amount of waving lotion by weight is applied to a weight of said essentially dry hair.

37. The method of claim 1, wherein applying a waving lotion to said essentially dry hair prior to the application of any further external moisture is performed at ambient temperature.

38. A method of straightening hair, comprising the steps of:

initiating said method of straightening hair by taking a body of hair, having an inherent moisture content of about 10% by weight;

applying a light mist of enhancer solution to the surface of said body of hair to facilitate subsequent processing of said hair without appreciably increasing the moisture content of said body of hair, said misted hair being essentially dry hair and containing no more than 20% water by weight;

applying a waving lotion to essentially dry hair prior to the application of any further external moisture;

applying tension to the hair having the applied waving lotion to obtain straightened hair; and said method of permanently straightening hair capable of application at all pH's with a pH range of 6.5 to 9.5.

39. The method of claim 38, wherein said waving lotion comprises at least one reducing agent.

40. The method of claim 38, wherein said waving lotion comprises at least one reducing agent selected from the group consisting of thioglycolic or thiolactic acids and their derivative salts and esters, cysteine and its derivatives, cysteamine and its derivatives, inorganic sulfites and bisulfites.

41. The method of claim 38, wherein said waving lotion includes at least one additive selected from the group consisting of chelating agents, cleansing herbs, anionic, amphoteric, or nonionic surfactants, anionic, cationic, or nonionic polymers, buffering agents, proteins, botanical extracts, amino acids and fragrances.

42. The method of claim 38, further comprising the steps of:

rinsing the hair with water;

blotting the hair with a towel; and neutralizing the hair with a neutralizer.

43. The method of claim 38, wherein said body of hair is returned to essentially dry condition prior to the application of said waving lotion.

44. The method of claim 38, wherein absorption of said waving lotion into said essentially dry hair is greater than 90% when an approximately equal amount of waving lotion by weight is applied to a weight of said essentially dry hair.

45. A method of permanently waving hair, comprising the steps of:

initiating said method of permanently waving hair by taking a body of hair, having an inherent moisture content of about 10% by weight;

applying a light mist of enhancer solution to the surface of said body of hair to facilitate subsequent wrapping of said hair without appreciably increasing the moisture content of said body of hair, said misted hair being essentially dry hair and containing no more than 20% water by weight;

wrapping said body of hair onto a plurality of wrapping devices;

applying a waving lotion to said essentially dry hair prior to the application of any further external moisture;

allowing said waving lotion to be in contact with said essentially dry hair for no more than 10 minutes; and processing the hair having the applied waving lotion to obtain permanently waved hair.

46. The method of claim 45, wherein said body of hair is returned to essentially dry condition prior to the application of said waving lotion.

47. The method of claim 45, wherein absorption of said waving lotion into said essentially dry hair is greater than 90% when an approximately equal amount of waving lotion by weight is applied to a weight of said essentially dry hair.

48. The method of claim 45, wherein applying a waving lotion to said essentially dry hair prior to the application of any further external moisture is performed at ambient temperature.

49. A method of straightening hair, comprising the steps of:

initiating said method of straightening hair by taking a body of hair, having an inherent moisture content of about 10% by weight;

applying a light mist of enhancer solution to the surface of said body of hair to facilitate subsequent processing of said hair without appreciably increasing the moisture content of said body of hair, said misted hair being essentially dry hair and containing no more than 20% water by weight;

applying a waving lotion to essentially dry hair prior to the application of any further external moisture;

allowing said waving lotion to be in contact with said essentially dry hair for no more than 10 minutes; and applying tension to the hair having the applied waving lotion to obtain straightened hair.

50. The method of claim 49, wherein said body of hair is returned to essentially dry condition prior to the application of said waving lotion.

51. The method of claim 49, wherein absorption of said waving lotion into said essentially dry hair is greater than 90% when an approximately equal amount of waving lotion by weight is applied to a weight of said essentially dry hair.

* * * * *

UNITED STATES PATENT AND TRADEMARK OFFICE
CERTIFICATE OF CORRECTION

PATENT NO. : 6,557,562 B2
DATED : May 6, 2003
INVENTOR(S) : Jayaseelan Rathnam

It is certified that error appears in the above-identified patent and that said Letters Patent is hereby corrected as shown below:

Column 4,
Lines 9 and 11, replace "penn" with -- perm --.
Line 18, replace "penning" with -- perming --.

Column 9,
Line 29, replace "penned" with -- permed --.

Column 10,
Line 25, replace "penned" with -- permed --.

Column 15,
Line 33, replace "out" with -- to about --.

Column 23,
Line 37, replace "perrned" with -- permed --.

Column 25,
Lines 36 and 38, replace "penned" with -- permed --.

Signed and Sealed this

Twenty-third Day of September, 2003

JAMES E. ROGAN
*Director of the United States Patent and Trademark Office*